US009921203B2

(12) United States Patent
Rogel et al.

(10) Patent No.: US 9,921,203 B2
(45) Date of Patent: *Mar. 20, 2018

(54) METHOD FOR PREDICTING SEDIMENT CONTENT OF A HYDROPROCESSED HYDROCARBON PRODUCT

(75) Inventors: Estrella Rogel, Orinda, CA (US); Cesar Ovalles, Walnut Creek, CA (US); Pak Leung, San Ramon, CA (US); Nan Chen, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 1275 days.

This patent is subject to a terminal disclaimer.

(21) Appl. No.: 13/294,566

(22) Filed: Nov. 11, 2011

(65) Prior Publication Data

US 2013/0124105 A1 May 16, 2013

(51) Int. Cl.
*G01N 31/00* (2006.01)
*G01N 33/28* (2006.01)
*G01N 30/86* (2006.01)
*G01N 30/88* (2006.01)

(52) U.S. Cl.
CPC ..... *G01N 33/2823* (2013.01); *G01N 33/2829* (2013.01); *G01N 30/8631* (2013.01); *G01N 2030/8854* (2013.01)

(58) Field of Classification Search
CPC ... G01N 33/2829; G01N 33/2823; G06G 7/75
USPC ........................................................ 702/25
See application file for complete search history.

(56) References Cited

U.S. PATENT DOCUMENTS

| | | | |
|---|---|---|---|
| 4,493,765 A | 1/1985 | Long et al. | |
| 4,628,204 A | 12/1986 | Maes | |
| 4,634,660 A | 1/1987 | Kingsley | |
| 4,865,740 A | 9/1989 | Nolte et al. | |
| 4,865,741 A | 9/1989 | Nolte et al. | |
| 4,988,446 A | 1/1991 | Haberman et al. | |
| 4,990,773 A | 2/1991 | Supernaw et al. | |
| 5,092,983 A | 3/1992 | Eppig et al. | |
| 5,574,215 A | 11/1996 | Hunger et al. | |
| 5,861,228 A | 1/1999 | Descales et al. | |
| 5,969,237 A | 10/1999 | Jones et al. | |
| 6,733,921 B2 | 5/2004 | Richter et al. | |
| 6,773,921 B1 | 8/2004 | Schabron et al. | |
| 7,648,836 B1 * | 1/2010 | Scott ..................... | G01N 22/00 422/416 |
| 7,875,464 B2 | 1/2011 | Schabron | |
| 8,241,920 B2 | 8/2012 | Schabron et al. | |
| 8,273,581 B2 | 9/2012 | Schabron et al. | |
| 8,367,425 B1 | 2/2013 | Schabron et al. | |
| 8,492,154 B1 | 7/2013 | Schabron et al. | |
| 8,530,240 B1 | 9/2013 | Schabron et al. | |
| 8,628,970 B1 | 1/2014 | Schabron et al. | |
| 9,353,317 B2 | 5/2016 | Schabron et al. | |
| 9,458,389 B1 | 10/2016 | Schabron et al. | |

| | | | |
|---|---|---|---|
| 2003/0211621 A1 | 11/2003 | Rovani et al. | |
| 2007/0048874 A1 | 3/2007 | Schabron et al. | |
| 2012/0160015 A1 * | 6/2012 | Ovalles ................ | G01N 30/88 73/61.52 |
| 2013/0124106 A1 * | 5/2013 | Rogel ................ | G01N 33/2823 702/25 |

FOREIGN PATENT DOCUMENTS

| | | |
|---|---|---|
| EP | 400989 | 5/1990 |
| WO | 00/77120 A2 | 12/2000 |
| WO | 00/77120 A3 | 12/2000 |
| WO | 02/063292 A1 | 8/2002 |
| WO | 03/096011 A1 | 11/2003 |
| WO | 2011/032123 | 3/2011 |
| WO | 2011/032125 | 3/2011 |
| WO | 2011/113017 | 9/2011 |

OTHER PUBLICATIONS

Du, James L. et al., "A Thermodynamic Model for the Prediction of Asphaltene Precipitation", Petroleum Science and Technology, 2004, vol. 22, No. 1-8 pp. 1023-1033.
PCT/US2012/060233, Notification of Transmittal of the International Search Report and the Written Opinion of the International Searching Authority, or the Declaration, dated Mar. 29, 2013, 11 pages.
Izquierdo, A., Carbogani, L., Leon, V., Parisi, A., Fuel Sci. Tech. Int. 7, 561 (1989).
Gray, M. R., Jokuty, P., Yeniova, H., Nazarewycz, L., Wanke, S. E., Achia, U., Krzywicki, A., Sanford, E. C., Sy, O. K. Y., Can. J. Chem. Eng. 69, 833 (1991).
Reynolds, J., Symposium on Correlation between Resid Characterization and Processability, presented before the Division of Petroleum Chemistry, American Chemical Society, Dallas, Apr. 9-14, 1989.
Gauthier, T., Quoineaud, A-A, Merdrignac, I., Energy & Fuels, 20, 2028 (2006).
Rogel, E., Carbognana, L., presented at the 1999 SPE Latin American and Caribbean Petroleum Engineering Conference held in Caracas, Venezuela, Apr. 21-23, 1999.

(Continued)

*Primary Examiner* — Michael Nghiem
(74) *Attorney, Agent, or Firm* — Ryan, Mason & Lewis, LLP (57) ABSTRACT

Disclosed herein is a method of predicting sediment content of a hydroprocessed hydrocarbon product. The method involves: (a) precipitating an amount of asphaltenes from a liquid sample of a first hydrocarbon-containing feedstock having solvated asphaltenes therein with one or more first solvents; (b) determining one or more solubility characteristics of the precipitated asphaltenes; (c) analyzing the one or more solubility characteristics; (d) determining asphaltene content of the liquid sample from the results of analyzing the one or more solubility characteristics; (e) determining one or more asphaltene stability parameters of the liquid sample from the results of analyzing the one or more solubility characteristics; and (f) correlating the asphaltene content and one of the asphaltene stability parameters of the liquid sample with at least two operation conditions associated with a refinery to predict sediment content.

9 Claims, 3 Drawing Sheets

(56) References Cited

OTHER PUBLICATIONS

Layrisse, I, Rivas, H., Acevedo, S., Rev. Tec. Intevep, 4, 3-18 (1984).
Nomura et al. Energy & Fuels, 13, 287 (1999).
Storm, D. A., Edwards, J. C., DeCanio, S. J., Sheu, E. Y., Energy & Fuels, 8, 561 (1994).
Murray, M. R. "Upgrading Petroleum Residues and Heavy Oil", Dekker, New York, (1994) and references therein.
Michael, G., Al-Siri, M., Khan, Z. H., A. Ali, F. A., Energy & Fuels, 19, 1598 (2005).
Boduszynski, M. M., Robbers, J. A., Chevron Document No. 8790158, Feb. 1987.
Boduszynski, M. M., Chevron Document No. CP9945530, Feb. 1987.
Clay, R. J., Boduszynski, M. M., Hubert, J. M., Chevron Document No. 879185, Dec. 1987.
Schabron, J. F.; Rovani, J. F., Fuel 87, 2008, 165.
Barton, A. F. M. Handbook of Solubility Parameters and Other Cohesion Parameters; CRC Pres Inc.: Boca Raton, FL, 1983 pp. 93.
Gray. M.R., Energy and Fuels, 17, 9. 1566 (2003).
U.S. Appl. No. 12/833,802, filed Mar. 2011, Roger et al.
U.S. Appl. No. 12/833,814, filed Mar. 2011, Roger et al.
Cortell, Jessica M. et al, "Influence of Vine Vigor on Grape (Vitisvinifera L. Cv. Pinot Noir) Anthocyanins. 2. Anthocyanins and Pigmented Polymers in Wine," J. Agric. Food Chem., 55, pp. 6585-6595 (2007).
Aske, Narve et al., "Determination of Saturate, Aromatic, Resin, and Asphaltenic (SARA) Components in Crude Oils by Means of Infrared and Near-Infrared Spectroscopy", Energy & Fuels, 15, pp. 1304-1312 (2001).
Bodusynski, M. M. et al, "Composition of heavy petroleums: I. Molecular weight, hydrogen deficiency, and heteroatom concentration as a function of atmospheric equivalent boiling point up to 1400° F.", Energy & Fuels, 1, pp. 2-11 (1987).
Corbett, L. W., "Composition of Asphalt Based on Generic Fractionation11111111111, Using Solvent Deasphaltening, Elution-Adsorption Chromatography, and Densimetric Characterization," Analytical Chemistry, p. 576, 1968.
Snyder, L.R., "Principles of Adsorption Chromatography", Marcel Dekker, Inc. New York, pp. 206-210, 1968.
Schabron, J. F. et al, "Initial studies using ultrasonic spectroscopy for monitoring changes in residua with pyrolysis", Fuel 85, pp. 2093-2105 (2006).
Chiantore, Oscar and Simonelli, Alessandra, "Precipitation-redissolution Liquid Chromatography of Styrene-ethyl Acrylate Copolymerskk", Polymer Engineering and Science, 39(8), pp. 1383-1388 (1999).
Bodusynski, M. M. et al., "Separation of Solvent-Refined Coal into Solvent-Derived Fractions", Analytical Chemistry, 54, pp. 372-375 (1982).
Burrell, H. "Solubility Parameters." Interchemical Review, pp. 3-16 (1955).
Carrier, H. et al, "Acoustic method for measuring asphaltene flocculation in crude oils", Journal of Petroleum Science and Engineering, pp. 11-117, 1999.
Schabron, J. F. et al, "Coking indexes using the Heithaus titration and asphaltene solubility", Preprints—American Chemical Society, Division of Petroleum Chemistry, 44(2), pp. 187-189 (1999).
Schabron, J. F. et al, "The Solubility and Three-Dimensional Structure of Asphaltenes", Petroleum Science and Technology, 16 (3-4), pp. 361-376 (1998).
Schabron, J. F. et al., "Petroleum Residua Solubility Parameter/Polarity Map: Stability Studies of Residua Pyrolysis," Department of Energy Report under contract # DE-FC26-98FT40322 Task pp. 1, 2, 24, (1999).
Schabron, J. F. et al, Molecular Weight/Polarity Map for Residua Pyrolysis, Fuel, 80(4), pp. 529-537, 2000.
Schabron, J. F. et al, "Non-Pyrolytic Heat Induced Deposition from Heavy Oils", Fuel, 80(7), p. 919-928 (2001).
Schabron, J. F. et al, "Residua Coke Formation Predictability Maps", Fuel 81,(17), pp. 2227-2240, 2002.
Schabron, J. F. et al, "Predicting Coke Formation Tendencies", Fuel 80(10) pp. 1435-1446 (2001).
Schabron, J. F. et al, "Characterization of Residua During Pyrolysis", Preprints, Div. of Petroleum Chemistry, American Chemical Society, 47(1), pp. 17-21 (2002).
Schabron, J. F. et al, "The Characterization of Petroleum Residua", U. S. Department of Energy under contract # DE-FC21-86MC110761, 68 pages (1993).
Schabron, J. F. et al, "Thermal Analysis for Monitoring Incipient Coke Formation", U. S. Department of Energy under contract # DE/FG36/01G011018, 18 pages (2002).
Schabron, J. F. et al, "Coke Formation Process Model for Petroleum Refining Efficiency Improvement", U. S. Department of Energy under contract # DE/FG36/01G011018, 40 pages (2002).
Singh, I. D et al., "Characteristic Changes of Asphaltenes During Visbreaking of North Gujarat Short Residue", Fuel, 69 (3), pp. 289-292 (1990).
Small, P.A., "Some Factors Affecting the Solubility of Polymers", Journal of Applied Chemistry, pp. 71-80 (1953).
"Standard Test Method n-Heptane Insulbles 1", Designation: D 3279-97 (Reapproved 2001).
"Energy and Environmental Profile of the US Petroleum Refining Industry", Prepared by Energetics Inc., for U.S. Department of Energy Office of Industrial Technologies (1988).
Schabron, J. F. et al, "Asphaltene Determinator Method for Automated On-Column Precipitation and Redissolution of Pericondensed Aromatic Asphaltene Components", Energy Fuels, (24), pp. 5984-5996, DOI: 10.102/ef100822f (2010).
Fan, T. et al., "Rapid and Accurate SARA Analysis of Medium Gravity Crude Oils", Energy & Fuels (16), pp. 1571-1575 (2002).
Schabron, J. F. et al, "On-column precipitation and re-dissolution of asphaltenes in petroleum residua", Fuel 87, pp. 165-176, (2008).
Grizzle, Patrick L., et al., "Automated Liquid Chromatographic Compound Class Grou-Type Separation of Crude Oils and Bitumens Using Chemically Bonded Aminosilane", Anal. Chem. (58), pp. 2389-2396 ((1986).
Jewell, D. M. et al., "Ion-Exchange, Coordination, and Adsorption Chromatographic Separation of Heavy-End Petroleum Distillates", Laramie Energy Research Center, Analytical Chemistry, 44(8), p. 1391 (Jul. 1972).
Karlsen, D. A. et al., "Analysis of petroleum fractions by TLC-FID: applications to pertroleum reservoir description", Org. Geochem 17(5), pp. 603-617 (1991).
Schabron, J. F. et al., Total Pericondensed Aromatic (TPA) Determination as an Alternative to Gravimetric Asphaltenes, Prepr. Pap.—Am. Chem. Soc. Div. Pet. Chem., 56(1), 38 (2001).
Rogel, E. et al., "Determination of Asphaltenes in Crude Oil and Petroleum Products by the on Column Precipitation Method", Energy Fuels, 23, pp. 4515-4521 (2009).
"Energy and Environmental Profile of the US Petroleum Refining Industry", Prepared by Energetics Inc. for U.S. Department of Energy Office of Industrial Technologies, pp. 4-5, 27, 33, 49 and 62-63.
"Standard Test Method for Molecular Weight (Relative Molecular Mass) of Hydrocarbons by Thermoelectric Measurement of Vapor Pressure," ASTM Designation: D 2503-82 (Reapproved 1997), pp. 871-873.
Anderson, S.I. et al., "Aggregation of Asphaltenes as Determined by Calorimetry", Journal of Colloid and Interface Science, 142, pp. 497-502 (1991).
Barton, A.F., "Solubility Parameters", Chemical Reviews, 75(6), pp. 731-753 (1974).
Magaril, R. Z. et al., Study of the Mechanism of Coke Formation in the Cracking of Petroleum Resins, International Chemical Engineering 8(4), p. 727, 1968.
M.M. Boduszynski et al., "Separation of Solvent-Refined Coal into Solvent-Derived Fractions," Analytical Chemistry, 1982, pp. 372-375, vol. 54, No. 3.
F.P. Burke et al., "Liquid Column Fractionation: A Method of Solvent Fractionation of Coal Liquefaction and Petroleum Products," Fuel, 1979, pp. 539-541, vol. 28, No. 7.

(56) References Cited

OTHER PUBLICATIONS

F.K. Schweighardt et al., "Evaluation of Analytical Techniques for SRC-1 Characterization, Recycle Solvent Studies, and Product Fractionation Studies: Development of SRC-1 Product Analysis," United States Department of Energy Technical Report No. DOE/OR/03054-61-vol. 2, Sep. 1983, pp. 250 and 276.
Barton, A. F. M. Handbook of Solubility Parameters and Other Cohesion Parameters; CRC Pres Inc.: Boca Raton, FL, (1983)—Table Hansen and Beerbower p. 96-103.
Barton, A. F. M. Handbook of Solubility Parameters and Other Cohesion Parameters; CRC Pres Inc.: Boca Raton, FL, (1983)—Table Hoy p. 123-138.
Barton, A. F. M. Handbook of Solubility Parameters and Other Cohesion Parameters; CRC Pres Inc.: Boca Raton, FL, (1983)—Gardon and Teas, p. 116-119.
Sundaram et al., "Thermodynamic Model of Sediment Deposition in the LC-FINING Process", Energy & Fuels 22, 3226-3236 (2008).
Irwin A. Wiehe, "Process Chemistry of Petroleum Macromolecules", Chemical Industries, Chapter 2, p. 293 (2008).
Schabron et al., Asphaltene Determinator Method for Automated On-Column Precipitation and redissolution of Percondensed Aromatic Asphaltene Components, Energy Fuels 2010, 24, 5984-5996.
Watkinson, et al, Fouling of a Sweet Crude Oil under Inert and Oxygenated Conditions, Energy & Fuels 2000, 14, 64-69.
Schabron et al., Residua coke formation predictability maps, Fuel 81 (2002) 2227-2240.
Sundaram et al., Thermodynamic Model of Sediment Deposition in the LC-FINING Process, Energy & Fuels 2008, 22, 3226-3236.
Rogel et al., Determination of Asphaltenes in Crude Oil and Petroleum Products by the on Column Precipitation Method, Energy Fuels 2009, 23, 4515-4521.
Storm, D.A., Decanio, S.J., Edwards, J.C., andSheu, E.Y., 1997, Sediment Formation During Heavy Oil Upgrading, Petroleum Science and Technology, 15(1&2), 77-102.

\* cited by examiner

METHOD FOR PREDICTING SEDIMENT CONTENT OF A HYDROPROCESSED HYDROCARBON PRODUCT

BACKGROUND OF THE INVENTION

1. Technical Field

The present invention generally relates to a method for predicting sediment content of a hydroprocessed hydrocarbon product.

2. Description of the Related Art

Presently, the petroleum industry relies more heavily on relatively high boiling feedstocks derived from materials such as coal, tar sands, oil-shale, and heavy crudes. These feedstocks generally contain significantly more undesirable components, especially from an environmental point of view. For example, such undesirable components include halides, metals and heteroatoms such as sulfur, nitrogen, and oxygen. Furthermore, specifications for fuels, lubricants, and chemical products, with respect to such undesirable components, are continually becoming stricter. Consequently, such feedstocks and product streams require more severe upgrading in order to reduce the content of such undesirable components. More severe upgrading, of course, adds considerably to the expense of processing these petroleum streams.

Hydroprocessing, which includes by way of example, hydroconversion, hydrocracking, hydrotreating, hydrogenation, hydrofinishing and hydroisomerization, plays an important role in upgrading petroleum feedstocks to meet the more stringent quality requirements. For example, there is an increasing demand for improved hetero-atom removal, aromatic saturation, and boiling point reduction as well as removal of metal contaminants such as vanadium and nickel. Much work is presently being done in hydrotreating because of greater demands for the removal of undesirable components such as heteroatoms, most notably sulfur, from transportation and heating fuel streams. Hydrotreating is well known in the art and usually involves treating the petroleum streams with hydrogen in the presence of a supported catalyst at hydrotreating conditions.

Hydrocarbon feedstocks likewise generally contain polar core materials, such as asphaltenes, dispersed in lower polarity solvent(s). Intermediate polarity material(s), usually referred to as resin(s), can associate with the polar core materials to maintain a homogeneous mixture of the components.

Asphaltenes are organic heterocyclic macromolecules which occur in crude oils. Under normal reservoir conditions, asphaltenes are usually stabilized in the crude oil by maltenes and resins that are chemically compatible with asphaltenes, but that have lower molecular weight. Polar regions of the maltenes and resins surround the asphaltene while non-polar regions are attracted to the oil phase. However, changes in pressure, temperature or concentration of the crude oil can alter the stability of the dispersion and increase the tendency of the asphaltenes to agglomerate into larger particles. As these asphaltene agglomerates grow, so does their tendency to precipitate out of solution.

One of the problems encountered during hydroprocessing (i.e., refining) is sediment formation. The formation of sediments is related to the asphaltene content in the residue. Sediment formed during hydroprocessing operations may settle and deposit in such apparatuses as the catalytic reactor, distillation units and heat exchangers in the fractionation section. This affects the overall economy of the system since the reactor system cannot reach higher conversions. The prevention or suppression of these coke-like sediment materials is therefore highly desirable. Presently, there are only a few ways to determine sediment forming tendencies, and they are time-consuming and have a low repeatability. For example, ASTM test method 4870 is used for the determination of total sediment in residual fuels. This test method is time consuming, has several sources of errors and requires constant operator's attention. It also has a limited application to those residues that can be filtered under the conditions of the method. However, the data obtained from this test method is used for making decisions about operation conditions, activity and life of the catalyst, use of additive, etc.

Accordingly, it would be advantageous to characterize a hydrocarbon-containing feedstock prior to subjecting it to hydroprocessing in order to evaluate its propensity for sediment production following hydroprocessing. Thus, it would be desirable to provide methods for predicting sediment content of a hydroprocessed hydrocarbon product that can be carried out in a simple, cost efficient and repeatable manner.

SUMMARY OF THE INVENTION

In accordance with one embodiment of the present invention, there is provided a method for predicting sediment content of a hydroprocessed hydrocarbon product comprising the steps of:

(a) precipitating an amount of asphaltenes from a liquid sample of a first hydrocarbon-containing feedstock having solvated asphaltenes therein with one or more first solvents in a column;

(b) determining one or more solubility characteristics of the precipitated asphaltenes;

(c) analyzing the one or more solubility characteristics of the precipitated asphaltenes;

(d) determining asphaltene content of the liquid sample from the results of analyzing the one or more solubility characteristics of the precipitated asphaltenes;

(e) determining one or more asphaltene stability parameters of the liquid sample from the results of analyzing the one or more solubility characteristics of the precipitated asphaltenes; and (f) correlating the asphaltene content and one of the asphaltene stability parameters of the liquid sample and at least two operation conditions associated with a refinery to predict sediment content of the hydroprocessed hydrocarbon product.

In accordance with a second embodiment of the present invention, there is provided a method comprising the steps of:

(a) precipitating an amount of asphaltenes from a liquid sample of a first hydrocarbon-containing feedstock having solvated asphaltenes therein with one or more first solvents in a column;

(b) determining one or more solubility characteristics of the precipitated asphaltenes;

(c) analyzing the one or more solubility characteristics of the precipitated asphaltenes;

(d) determining asphaltene content of the liquid sample from the results of analyzing the one or more solubility characteristics of the precipitated asphaltenes;

(e) determining one or more asphaltene stability parameters of the liquid sample from the results of analyzing the one or more solubility characteristics of the precipitated asphaltenes;

(f) correlating the asphaltene content and one of the asphaltene stability parameters of the liquid sample and at least two operation conditions associated with a refinery to predict sediment content of a hydroprocessed hydrocarbon product; and (g) selecting a second hydrocarbon-containing feedstock sample; repeating steps (a)-(f); and comparing the sediment content prediction of the second sample with the sediment content prediction of the first sample to predict a leading candidate hydroprocessed hydrocarbon product.

In accordance with a third embodiment of the present invention, there is provided a method comprising the steps of:

(a) precipitating an amount of asphaltenes from a liquid sample of a first hydrocarbon-containing feedstock having solvated asphaltenes therein with one or more first solvents in a column;

(b) determining one or more solubility characteristics of the precipitated asphaltenes;

(c) analyzing the one or more solubility characteristics of the precipitated asphaltenes;

(d) determining asphaltene content of the liquid sample from the results of analyzing the one or more solubility characteristics of the precipitated asphaltenes;

(e) determining one or more asphaltene stability parameters of the liquid sample from the results of analyzing the one or more solubility characteristics of the precipitated asphaltenes;

(f) correlating the asphaltene content and one of the asphaltene stability parameters of the liquid sample and at least two operation conditions associated with a refinery to predict sediment content of a hydroprocessed hydrocarbon product; and (g) selecting a different sample of the same first hydrocarbon-containing feedstock sample; repeating steps (a)-(f); and comparing the sediment content prediction of the different sample with the sediment content prediction of the first sample.

In accordance with a fourth embodiment of the present invention, there is provided a method comprising the steps of:

(a) selecting one or more hydrocarbon-containing feedstocks, wherein the selection of the one or more hydrocarbon-containing feedstocks comprises:
  (i) precipitating an amount of asphaltenes from a liquid sample of a first hydrocarbon-containing feedstock having solvated asphaltenes therein with one or more first solvents in a column;
  (ii) determining one or more solubility characteristics of the precipitated asphaltenes;
  (iii) analyzing the one or more solubility characteristics of the precipitated asphaltenes;
  (iv) determining asphaltene content of the liquid sample from the results of analyzing the one or more solubility characteristics of the precipitated asphaltenes;
  (v) determining one or more asphaltene stability parameters of the liquid sample from the results of analyzing the one or more solubility characteristics of the precipitated asphaltenes; and
  (vi) correlating the asphaltene content and one of the asphaltene stability parameters of the liquid sample and at least two operation conditions associated with a refinery to predict sediment content of a hydroprocessed hydrocarbon product; and (b) feeding the selected one or more hydrocarbon-containing feedstocks to one or more crude hydrocarbon refinery components.

In accordance with a fifth embodiment of the present invention, there is provided a system comprising: (a) one or more crude hydrocarbon components; and (b) one or more hydrocarbon-containing feedstocks in fluid communication with the one or more crude hydrocarbon refinery components, wherein the one or more hydrocarbon-containing feedstocks are selected by a process comprising:
  (i) precipitating an amount of asphaltenes from a liquid sample of a first hydrocarbon-containing feedstock having solvated asphaltenes therein with one or more first solvents in a column;
  (ii) determining one or more solubility characteristics of the precipitated asphaltenes;
  (iii) analyzing the one or more solubility characteristics of the precipitated asphaltenes;
  (iv) determining asphaltene content of the liquid sample from the results of analyzing the one or more solubility characteristics of the precipitated asphaltenes;
  (v) determining one or more asphaltene stability parameters of the liquid sample from the results of analyzing the one or more solubility characteristics of the precipitated asphaltenes; and
  (vi) correlating the asphaltene content and one of the asphaltene stability parameters of the liquid sample and at least two operation conditions associated with a refinery to predict sediment content of a hydroprocessed hydrocarbon product.

The methods of the present invention advantageously predict the sediment propensity of a hydrocarbon-containing feedstock following hydroprocessing, i.e., a hydroprocessed hydrocarbon product, in a simple, cost efficient and repeatable manner. In this manner, a leading candidate hydrocarbon-containing feedstock can be readily characterized by its potential to produce sediment. Based on this prediction, it is also possible to adjust refinery operation conditions such as, for example, temperature, catalyst amount, etc, in order to minimize fouling during hydroprocessing. Also, by predicting the sediment content of the resulting product based on the feed, it is possible to design blending strategies and adjust refinery operation conditions for further processing with minimal fouling. Furthermore, quality control of new batches of feedstocks and in blending raw materials can be achieved without affecting refinery operation conditions.

DETAILED DESCRIPTION OF THE PREFERRED EMBODIMENTS

In one embodiment, a method for predicting sediment content of a hydroprocessed hydrocarbon product of the present invention involves (a) precipitating an amount of asphaltenes from a liquid sample of a first hydrocarbon-containing feedstock having solvated asphaltenes therein with one or more first solvents in a column; (b) determining one or more solubility characteristics of the precipitated asphaltenes; (c) analyzing the one or more solubility characteristics of the precipitated asphaltenes; (d) determining asphaltene content of the liquid sample from the results of analyzing the one or more solubility characteristics of the precipitated asphaltenes; (e) determining one or more asphaltene stability parameters of the liquid sample from the results of analyzing the one or more solubility characteristics of the precipitated asphaltenes; and (f) correlating the asphaltene content and one of the asphaltene stability parameters of the liquid sample and at least two operation conditions associated with a refinery to predict sediment content of the hydroprocessed hydrocarbon product. In this manner, a hydrocarbon-containing feedstock can be characterized for its propensity for sediment formation after being hydroprocessed. This way, the hydroprocessing conditions may be modified in order to decrease the propensity of the hydrocarbon-containing feedstock for sediment formation after being hydroprocessed. Alternatively, the proposed hydrocarbon-containing feedstock can be discarded and a leading hydrocarbon-containing feedstock can be chosen for hydroprocessing.

Generally, the source of the hydrocarbon-containing feedstock having solvated asphaltenes therein may be any source where such a hydrocarbon crude may be obtained, produced, or the like. The source may be one or more producing wells in fluid communication with a subterranean oil reservoir. The producing well(s) may be under thermal recovery conditions, or the producing well(s) may be in a heavy oil field where the hydrocarbon crude or oil is being produced from a reservoir having a strong water-drive.

In one embodiment, the hydrocarbon-containing feedstock sample includes any heavy hydrocarbons such as heavy crude oil, heavy hydrocarbons extracted from tar sands, commonly called tar sand bitumen, such as Athabasca tar sand bitumen obtained from Canada, heavy petroleum crude oils such as Venezuelan Orinoco heavy oil belt crudes, Boscan heavy oil, Hamaca crude oil, heavy hydrocarbon fractions obtained from crude petroleum oils, particularly heavy vacuum gas oils, atmospheric residue, vacuum residuum as well as petroleum tar, tar sands and coal tar. Other examples of heavy hydrocarbon feedstocks which can be used are oil shale, shale, coal liquefaction products and the like.

In another embodiment, the hydrocarbon-containing feedstock sample includes any solid hydrocarbon-containing deposit such as asphaltene solids from, e.g., refinery production preparation or an oil facility.

In another embodiment, the hydrocarbon-containing feedstock sample includes any processed sample such as heavy cycle gas oil (HCGO), LC Fining ebullated bed hydrocracking products, fluid catalytic cracking (FCC) products and the like.

In general, a liquid sample of a first hydrocarbon-containing feedstock having solvated asphaltenes therein is first provided. As one skilled in the art will readily understand, it may be necessary to add a solvent to the hydrocarbon-containing feedstock in order for the sample to be sufficiently fluid enough to be passed through the column. Useful solvents include any solvent in which the hydrocarbon-containing feedstock sample is soluble or which is capable of allowing the hydrocarbon-containing feedstock sample to be sufficiently fluid to be passed through the column. Representative examples of such solvents include one or more chlorinated hydrocarbon solvents, one or more aromatic hydrocarbon solvents, one or more ether solvents, one or more alcohol solvents and the like and mixtures thereof.

Suitable chlorinated hydrocarbon solvents include, but are not limited to, dichloromethane, 1,2-dichloroethane, chloroform, carbon tetrachloride and the like and mixtures thereof. Suitable aromatic hydrocarbon solvents include, but are not limited to, benzene, toluene, xylene and the like and mixtures thereof. Suitable ether solvents include tetrahydrofuran, diethylether, dioxane and the like and mixtures thereof. Suitable alcohol solvents include low molecular weight aliphatic alcohols such as methanol, ethanol, isopropanol and the like and mixtures thereof.

In one embodiment, the sample solution can be prepared from about 10 to about 50 wt. % solution of the hydrocarbon-containing feedstock sample in the solvent(s).

Initially, at least a portion of the sample solution is injected into a column. Generally, the column will have an inlet and an outlet and can be any type of column which is hollow and permits the flow of an aqueous-type material through the interior of the column. The column can be any size and cross sectional shape, e.g., the column can be cylindrical, square, rectangular, triangular, or any other geometrical shape as long as it is hollow and permits the passing of aqueous-type material. In one embodiment, the column is cylindrical. Furthermore, the column can be of any suitable length and any inner diameter or inner cross-sectional area. In one embodiment, the column can have a diameter of from about 0.25 inches (0.64 cm) to about 1 inch (2.5 cm) and a length of from about 50 mm to about 500 mm. One skilled the art could envisage that the column can generally be any inert filtration device for use the methods of the present invention.

Any suitable material may be selected for use as the column. For example, the column can be formed of a relatively inert or chemically unreactive material such as glass, stainless steel, polyethylene, polytetrafluoroethylene (PTFE), polyaryletheretherketone, (PEEK), silicon carbide or mixtures of thereof, for example, a PEEK-lined stainless steel column.

The column may be vertical or horizontal or arranged in any suitable way, provided that it can be loaded with the sample solution and that the appropriate solvent(s) can be passed through it. As will be understood by those of ordinary skill in the art, a pump may also be used to increase the flow rate through the column.

In another embodiment, an inert packing material is included within the column. The amount of the inert packing material should not exceed an amount which will prevent the passing of any liquid containing material through the column. The packed column advantageously allows for the use of a relatively small volume of sample solution and solvent(s). Suitable inert packing material includes any material that is inert to asphaltene irreversible adsorption. Examples of such materials include fluorinated polymers such as, for example, polyvinylidene fluoride (PVDF), fluorinated ethylene propylene (FEP), polytetrafluoroethylene (PTFE), silicon carbide, polydivinylbenzene (PDVB) and the like and mixtures thereof.

Once the sample solution has been passed into the column, one or more first solvents are then passed through the column. Useful one or more first solvents are typically alkane mobile phase solvent(s) and can be determined by one skilled in the art. In one embodiment, the alkane mobile phase solvent is n-heptane. However, other alkane mobile phase solvents such as, for example, iso-octane, n-pentane or n-hexane may be used.

The one or more first solvents should be passed into the column for a time period sufficient to elute the alkane soluble fraction, commonly known as maltenes or petrolenes, and induce precipitation of the alkane insoluble fraction, i.e., the precipitated asphaltenes, from the hydrocarbon-containing feedstock sample. Generally, once the alkane mobile phase solvent (i.e., one or more first solvents) enters the column, the alkane mobile phase solvent dilutes and displaces the solvent in the sample solution, thereby allowing the asphaltenes to substantially precipitate therefrom. The alkane soluble fraction then elutes from the column.

In accordance with the present invention, one or more solubility characteristics of the precipitated asphaltenes are determined once substantially all of the alkane soluble fraction has eluted. The one or more solubility characteristics of the precipitated asphaltenes to be determined include, by way of example, solubility parameters, miscibility numbers, kauri-butanol numbers, dipole moments, relative permitivities, polarity indexes, refractive indexes and specific types of intermolecular interaction in liquid media such as acid and base numbers. Various ways to determine the one or more solubility characteristics of the precipitated asphaltenes are within the purview of one skilled in the art. For example, solubility characteristics of the precipitated asphaltenes can be determined according to the following methods: (1) Solubility Fraction Method; and (2) Solubility Profile Method.

Solubility Fraction Method

The solubility fraction method involves the step of determining one or more solubility characteristics of the precipitated asphaltenes by (1) dissolving at least part of the amount of the precipitated asphaltenes in one or more second solvents having a solubility parameter at least about 0.7 $MPa^{0.5}$ higher than the one or more first solvents; and (2) dissolving a second amount of the precipitated asphaltenes in one or more third solvents having a solubility parameter higher than the one or more second solvents, wherein the solubility parameter of the one or more third solvents is at least about 21 $MPa^{0.5}$ but no greater than about 30 $MPa^{0.5}$. A solubility parameter as described herein is determined by the Hansen's methodology described in Barton, A. F. M. *Handbook of Solubility Parameters and Other Cohesion Parameters*; CRC Pres Inc.: Boca Raton, Fla., p. 95 (1983).

Suitable one or more second solvents having a solubility parameter at least about 0.7 $MPa^{0.5}$ higher than the one or more first solvents can be determined by one skilled in the art. Useful solvents include, but are not limited to, one or more alkane solvents, one or more chlorinated hydrocarbon solvents, one or more aromatic solvents, one or more ether solvents, one or more alcohol, solvents and the like and mixtures thereof. Representative examples of such solvents can be any of those disclosed above. It is also contemplated that blends of such solvents can be used. In one embodiment, a blend can contain from about 0.5 wt. % to about 99.5 wt. % chlorinated solvent and from about 99.5 wt. % to about 0.5 wt. % alkane solvent. In another embodiment, a blend can contain from about 10 wt. % to about 25 wt. % chlorinated solvent and from about 90 wt. % to about 75 wt. % alkane solvent.

Suitable one or more third solvents having a solubility parameter higher than the one or more second solvents, wherein the solubility parameter of the one or more third solvents is at least about 21 $MPa^{0.5}$ but no greater than about 30 $MPa^{0.5}$, can be determined by one skilled in the art. Generally, the one or more third solvents will dissolve any remaining precipitated asphaltenes in the column. Useful solvents include, but are not limited to, one or more alcohol solvents, one or more chlorinated hydrocarbon solvents, one or more aromatic solvents, one or more ether second solvents and the like and mixtures thereof. Representative examples of such solvents can be any of those disclosed above. It is also contemplated that blends of such solvents can be used. In one embodiment, a blend can contain from about 0.5 wt. % to about 99.5 wt. % chlorinated solvent and from about 99.5 wt. % to about 0.5 wt. % alcohol solvent. In another embodiment, a blend can contain from about 80 wt. % to about 95 wt. % chlorinated solvent and from about 20 wt. % to about 5 wt. % alcohol solvent.

If desired, one or more additional solvents or solvent blends can be added to dissolve at least part of the amount of the precipitated asphaltenes after the addition of the one or more second solvents and before the addition of the one or more third solvents. In general, the one or more additional solvents or solvent blends will have a solubility parameter greater than the previously added one or more solvents or solvent blends and less than the solubility parameter of the one or more third solvents. For example, one or more fourth solvents having a solubility parameter between the solubility parameter of the one or more second solvents and the solubility parameter of the one or more third solvents can be added to dissolve at least part of the amount of the precipitated asphaltenes. In another embodiment, one or more fifth solvents having a solubility parameter between the solubility parameter of the one or more fourth solvents and the solubility parameter of the one or more third solvents can be added to dissolve at least part of the amount of the precipitated asphaltenes. In yet another embodiment, one or more sixth solvents having a solubility parameter between the solubility parameter of the one or more fifth solvents and the solubility parameter of the one or more third solvents can be added to the dissolve at least part of the amount of the precipitated asphaltenes.

Suitable additional solvents include, but are not limited to, one or more alkane solvents, one or more chlorinated hydrocarbon solvents, one or more alcohol solvents, one or more aromatic solvents and the like and mixtures thereof. Representative examples of such solvents can be any of those disclosed above.

The asphaltene concentration in the eluted fractions from the column is continuously monitored using, for example, a liquid chromatography detector which generates a signal proportional to the amount of each eluted fraction and is recorded in a manner well known in the art. There are a number of commercially available liquid chromatography detectors that can be used including, e.g., refractive index detectors, mass spectrometry, liquid chromatography/mass spectrometry, NMR spectroscopy, Raman spectroscopy, infrared spectroscopy, fluorescence spectroscopy, UV-Vis spectroscopy, diode array detector, Charged Aerosol, evaporative light scattering detectors (ELSD) and the like; all of which can be used in the methods described herein. Other online detectors are known to those skilled in the art. Quantification can then be performed using methods known in the art, e.g., using commercially-available computer programs.

In one preferred embodiment, an evaporative light scattering detector is used as a liquid chromatography detector to monitor each eluting sample's concentration to determine the solubility characteristics of the precipitated asphaltenes. The operating principle of an evaporative light scattering detector is as follows: the compounds to be analyzed are transported by a mobile phase or a more volatile carrier liquid which is then nebulized and evaporated at a relatively low temperature (being able to be in the order of from about 30 to about 150° C.) so that residual micro-particles alone remain—ideally the compounds to be analyzed—which can be detected by light scattering. In this manner, it is possible to analyze directly effluents which originate from the column under the condition of selecting a mobile phase which is volatile enough to be directly used as a carrier liquid for the evaporative light scattering detector. For example, in the case of the asphaltenes for the asphaltene fraction method, the result is a single peak for each eluted solvent fraction with each peak representing a solubility characteristic of the asphaltenes.

Solubility Profile Method

The solubility profile method involves the step of determining one or more solubility characteristics of the precipitated asphaltenes by dissolving a first amount and a second amount of the precipitated asphaltenes by gradually and continuously changing the alkane mobile phase solvent to a final mobile phase solvent having a solubility parameter at least about 1 $MPa^{0.5}$ higher than the alkane mobile phase solvent. Generally, the first amount of the precipitated asphaltenes (also referred to as "easy to dissolve asphaltenes") will have a lower solubility parameter than the second amount of asphaltenes (also referred to as "hard to dissolve asphaltenes"). The term "gradually" as used herein shall be understood to mean that the alkane mobile phase solvent is incrementally removed from the column over a period of time by continuously adding a final mobile phase solvent having a solubility parameter at least about 1 $MPa^{0.5}$ higher than the alkane mobile phase solvent to the column. Generally, gradually and continuously changing from essentially the alkane mobile phase solvent to the final mobile phase solvent can occur during a period of about 5 minutes to about 120 minutes at a flow rate of about 1 mL/min. to about 4 mL/min. In one embodiment, gradually and continuously changing from the alkane mobile phase solvent to the final mobile phase solvent can occur during a period of about 15 minutes to about 30 minutes at a flow rate of about 1 mL/min. to about 4 mL/min.

The first amount of the precipitated asphaltenes are dissolved by gradually and continuously changing the alkane mobile phase solvent to a first final mobile phase solvent having a solubility parameter at least about 1 $MPa^{0.5}$ higher than the alkane mobile phase solvent. As one skilled in the art will readily appreciate, the selection of the first final mobile phase solvent will depend on such factors as moving from a low solubility parameter solvent (low solvent power) to a high solubility parameter solvent (high solvent power) using solvents that have the right combination of dispersion, polar and hydrogen bonding forces. For example, a first final mobile phase solvent such as a chlorinated hydrocarbon solvent, e.g., dichloromethane, an ether solvent, an aromatic hydrocarbon solvent or mixtures thereof is gradually and continuously added to the column to sequentially change the alkane mobile phase solvent from 100% alkane mobile phase, solvent to 100% first final mobile phase solvent, i.e., the alkane mobile phase solvent is changed to 1% dichloromethane in 99% alkane mobile phase solvent, then to 2% dichloromethane in 98% alkane mobile phase solvent, until the mobile phase solvent in the column is 100% dichloromethane and 0% alkane mobile phase solvent. In this manner, a first amount of the precipitated asphaltenes (i.e., easy to dissolve asphaltenes) will be gradually dissolved and a characteristic elution pattern generated, which is referred to as the asphaltene solubility profile, as discussed hereinbelow.

After the first amount of precipitated asphaltenes has been gradually dissolved, a second or remaining amount of the precipitated asphaltenes (which are not capable of being redissolved in the one or more first final mobile phase solvents) is left in the column. Thus, in order to redissolve the second amount of precipitated asphaltenes, also referred to as hard to dissolve asphaltenes (i.e., higher solubility parameter asphaltenes), it is may be necessary to add one or more second final mobile phase solvents having a solubility parameter at least about 1 $MPa^{0.5}$ higher than the first final mobile phase solvent to the column in order to substantially dissolve the remaining amount of the precipitated asphaltenes in the column and generate a characteristic elution pattern of the hydrocarbon-containing feedstock. This can advantageously allow for a more accurate determination of the solubility profile of the various asphaltene components in the hydrocarbon-containing feedstock.

The selection of the second final mobile phase solvent will depend on such factors as moving from a lower solubility parameter solvent (the first final mobile phase solvent) to a higher solubility parameter solvent (the second final mobile phase solvent) using solvents that have the right combination of dispersion, polar and hydrogen bonding forces. A suitable one or more second final mobile phase solvent can readily be determined by one skilled in the art, e.g., a $C_1$ to $C_6$ alcohol such as methanol. Accordingly, in one embodiment, methanol is gradually and continuously added to the column to sequentially change the first final mobile phase solvent, e.g., dichloromethane, from 100% dichloromethane to 100% methanol, i.e., dichloromethane is first changed to 1% methanol in 99% dichloromethane, then to 2% methanol in 98% dichloromethane, until the second final mobile phase solvent in the column is 100% methanol and 0% dichloromethane.

The flow rate and time period for gradually and continuously adding the one or more second final mobile phase solvents are substantially the same as for the first final mobile phase solvents.

The asphaltene concentration in the eluted fractions from the column is continuously monitored using, for example, a liquid chromatography detector as discussed hereinabove. In one preferred embodiment, an evaporative light scattering detector is used as a liquid chromatography detector to monitor each eluting sample's concentration. The operating principle of an evaporative light scattering detector is as follows: the compounds to be analyzed are transported by a mobile phase or a more volatile carrier liquid which is then nebulized and evaporated at a relatively low temperature (being able to be in the order of from about 30 to about 150° C.) so that residual micro-particles alone remain—ideally the compounds to be analyzed—which can be detected by light scattering. In this manner, it is possible to analyze directly effluents which originate from the column under the condition of selecting a mobile phase which is volatile enough to be directly used as a carrier liquid for the evaporative light scattering detector. For example, in the case of the asphaltenes, the result is a curve that represents the solubility parameter distribution of the asphaltenes.

Next, a solubility profile of the asphaltenes in the liquid sample can be created by techniques known in the art. For example, when asphaltenes are quantified using an evaporative light scattering detector, the result is a curve that represents the solubility parameter distribution of the asphaltene in the hydrocarbon-containing feedstock. Since the solubility parameter of a mixture of solvents is given by the volumetric average of the components, it is possible to convert the time scale of the elution to a solubility parameter scale using the following equation:

$$\delta = \sum_{i=1}^{n} \phi_i \delta_i$$

wherein δ is the solubility profile of the mixture, $\phi_i$ is the volume fraction and $\delta_i$ is the solubility parameter of each of the components, respectively. The volume fraction is the volume fraction of the blend of each solvent and readily determined by the chromatography apparatus. The solubility parameter of a component is either known in the art, e.g., Barton, A. F. M. *Handbook of Solubility Parameters and Other Cohesion Parameters*; CRC Press Inc.: Boca Raton, Fla., 1983, or can be determined by techniques within the purview of one skilled in the art.

Determining Asphaltene Content

Once the one or more solubility characteristics have been analyzed for a given hydrocarbon-containing feedstock sample, the asphaltene content can be determined as follows.

Solubility Fraction Method

In the solubility fraction method, the result is one peak for each eluted solvent fraction with each peak representing a solubility characteristic of the asphaltenes. The area under the separate peaks can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Then, each area is correlated to an asphaltene mass according to a calibration curve that depends on the type of detector used as within the purview of one skilled in the art. The calibration may or may not be the same for all the peaks. The total asphaltene mass (TAM) for the sample would therefore be the addition of all the asphaltene masses (M) determined for each peak:

$$TAM = \sum_{i=1}^{n} M_i$$

Solubility Profile Method

In the solubility profile method, the amount of asphaltenes is determined by calculating the area of the second peak of the solubility profile. An asphaltene solubility profile normally shows either two peaks or one peak and one shoulder from the evaporative light scattering detector. The two peaks or peak/shoulder can be separated by numerical methods well known in the art such as, for example, peak deconvolution or peak fitting. The area under the peaks, e.g., the second peak, can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Then, this area is correlated to an asphaltene mass according to a calibration curve. A calibration procedure was developed that relates the measured peak area (A) to the total asphaltene mass in the sample (TAM). The following equation is an example of such correlation that allows the calculation of the asphaltene mass:

Log TAM=0.5336 log $A$−6.097 where TAM is the total asphaltene mass in the sample and A is the area of the second deconvoluted peak respectively.

Determining Asphaltene Stability

In one embodiment, an asphaltene stability parameter can be determined from the solubility characteristics of the asphaltenes in the hydrocarbon-containing feedstock sample from the solubility fraction method discussed above. The asphaltene fraction method normally shows a single peak for each eluted solvent fraction from the evaporative light scattering detector which represents the solubility characteristics of the asphaltenes. In one embodiment, the asphaltene stability can be determined from a ratio of the area under the single peaks for each eluted solvent fraction, i.e., once the peaks are known, the areas for each of the peaks are calculated and a ratio between the areas determined. The area under the peaks can be calculated using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Accordingly, one such way to calculate the ratio is as follows:

Ratio=(area peak 3+area peak 4)/(area peak 1+area peak 2)

wherein peak 1 is the first peak characterizing the first asphaltene fraction eluted from the column (i.e., easy to dissolve asphaltenes); peak 2 is the second peak characterizing the second asphaltene fraction eluted from the column; peak 3 is the third peak characterizing the third asphaltene fraction eluted from the column and peak 4 is the fourth peak characterizing the fourth asphaltene fraction eluted from the column. In this ratio, the first two peaks (peak 1 and 2) represent "easy to dissolve asphaltenes" that help in the solubilization of the rest of asphaltenes (last two peaks: 3 and 4) also known as "difficult to dissolve asphaltenes". The larger the ratio, the lower the stability since there are less easy to dissolve asphaltenes that help in the solubilization of the difficult to dissolve asphaltenes.

In another embodiment, asphaltene stability can be determined from the solubility profile of the asphaltenes in the hydrocarbon-containing feedstock sample created by the solubility profile method discussed above. For example, one or more parameters can be mathematically calculated based on the solubility profile of the asphaltenes. An asphaltene solubility profile normally shows either two peaks or one peak and one shoulder from the evaporative light scattering detector. The two peaks or peak/shoulder can be separated by numerical methods well known in the art such as, for example, peak deconvolution or peak fitting. The first resolved peak is generally known as an "easy to dissolve asphaltene" peak and is derived from step (i) which gradually and continuously changes the one or more first solvents to a first final mobile phase solvent having a solubility parameter at least about 1 MPa$^{0.5}$ higher than the one or more first solvents to dissolve a first amount of the precipitated asphaltenes. The second resolved peak or shoulder is generally known as a "hard to dissolve asphaltene" peak and is derived from step (ii) which gradually and continuously changes the first final mobile phase solvent to a second final mobile phase solvent having a solubility parameter at least about 1 MPa$^{0.5}$ higher than the first final mobile phase solvent to dissolve a second, or remaining amount of precipitated asphaltenes.

Examples of parameters related to asphaltene stability that can be calculated include the following.

1. Average solubility parameter of the hard to dissolve asphaltenes (SPA). This is a measurement of how difficult it is to dissolve the material eluted in the second peak or shoulder of the solubility profile (i.e., the hard to dissolve asphaltenes). It is calculated as the mean of the distribution corresponding to the second peak or shoulder obtained by the solubility parameter scale calculation discussed above. The higher the value, the more difficult it is to dissolve the hard to dissolve asphaltenes thereby indicating lower stability.

2. Ratio of hard-to-dissolve asphaltenes/easy to dissolve asphaltenes (i.e., second peak area/first peak area ratio wherein the second peak area and first peak area are derived from the solubility profile). After the separation of the peaks discussed hereinabove with respect to the asphaltene solubility profile, the areas for both peaks are calculated and the ratio between both areas determined. The area under the peaks can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). This ratio indicates whether there is enough transitional material or easy to dissolve asphaltenes (first peak) to keep the hard to dissolve (i.e., highly insoluble) asphaltenes (second peak) in solution. Accordingly, a larger ratio indicates a lower amount of transitional material or easy to dissolve asphaltenes present in the hydrocarbon-containing material in comparison with the more polar asphaltenes and hence a higher tendency of the latter to precipitate.

3. Overlapping of hard-to-dissolve asphaltenes to the easy to dissolve asphaltenes. This is a measurement of the compatibility between both species and, therefore, can be used to evaluate stability. After the separation of the peaks discussed hereinabove with respect to the asphaltene solubility profile, the area of both peaks are calculated as well as the overlapping area which corresponds with the area that both peaks share and lie in the same region. Accordingly, a higher value indicates greater stability and, therefore, the asphaltenes are less prone to precipitate.

4. ΔPS measures the broadness of the solubility profile and it is also related to the stability of the asphaltenes in the hydrocarbon-containing feedstock. This parameter is calculated according to the following equation:

$$\Delta PS = t(75\%) - t(25\%)$$

wherein t(75%) and t(25%) represent the time at which 75% and 25% of the asphaltenes in the hydrocarbon-containing feedstock (in terms of area) have eluted, respectively. The ΔPS is calculated based on the cumulative areas of the whole distribution of times or solubility parameters that represent the solubility profile of the asphaltenes in the sample. Accordingly, a higher value indicates that a higher solubility parameter solvent is required to redissolved them and hence they present a lower stability and are more prone to precipitate.

In another embodiment, asphaltene stability can be determined from the solubility characteristics of the asphaltenes in the hydrocarbon-containing feedstock sample according to ASTM D6703 or similar titration techniques well known by those skilled in the art., e.g., ASTM D7060, ASTM D4740, ASTM D7061, ASTM D7112 and ASTM D7157 These techniques provide the overall compatibility of the system. For example, ASTM D 6703 shows how to calculate P-value, which represent the stability. The larger this value, the more stable is the sample.

Predicting Sediment Content

Once the asphaltene content and one of the parameters related to asphaltene stability have been determined for a given hydrocarbon-containing feedstock sample, the propensity for sediment formation of the hydrocarbon-containing feedstock following hydroprocessing, i.e., the hydroprocessed hydrocarbon product, can be predicted by correlating the asphaltene content and one of the asphaltene stability parameters of the liquid sample together with at least two operation conditions associated with a refinery. As one skilled in the art would readily appreciate, operation conditions are those conditions associated with operating a refinery for hydroprocessing of a hydrocarbon-containing feedstock. Refinery operating conditions for hydroprocessing of hydrocarbon-containing feedstocks, e.g., heavy hydrocarbon streams such as petroleum hydrocarbon residua and the like, are well known in the art. Typical operation conditions associated with a refinery include temperature of the reactor, pressure of the reactor, feed liquid hourly space velocity (LHSV), gas flow of hydrogen, residuum conversion and cut point of the residue.

In general, refinery operation conditions comprise a pressure within the range of about 1,000 psia (68 atm) to about 3,000 psia (204 atm), an average catalyst bed temperature within the range of about 700 F (371 C) to about 850 F (454 C), a LHSV within the range of about 0.1 volume of hydrocarbon per hour per volume of catalyst to about 5 volumes of hydrocarbon per hour per volume of catalyst, and a hydrogen recycle rate or hydrogen addition rate within the range of about 2,000 standard cubic feet per barrel (SCFB) (356 m$^3$/m$^3$) to about 15,000 SCFB (2,671 m$^3$/m$^3$). In one embodiment, refinery operating conditions comprise a total pressure within the range of about 1,200 psia to about 2,000 psia (81-136 atm); an average catalyst bed temperature within the range of about 730° F. (387° C.) to about 820° F. (437° C.); and a LHSV within the range of about 0.1 to about 4.0; and a hydrogen recycle rate or hydrogen addition rate within the range of about 5,000 SCFB (890 m$^3$/m$^3$) to about 10,000 SCFB (1,781 m$^3$/m$^3$). Generally, the process temperatures and space velocities are selected so that at least 30 vol. % of the feed fraction boiling above 1,000° F. is converted to a product boiling below 1,000° F., more preferably at least 50 vol. % is converted to a product boiling below 1,000° F., and still more preferably so that at least 70 vol. % of the subject fraction is converted to a product boiling below 1,000° F.

The definition of residuum conversion (residuum is defined as feed fraction that has boiling point greater than 1000° F.):

Percent conversion for all parameters is calculated using the following equation:

$$[(\text{amount } X \text{ in feed} - \text{amount } X \text{ in product})/\text{amount } X \text{ in feed}]*100$$

For example, in the case of 1000° F.+ conversion in percent, it would be the volume of 1000° F.+ boiling material in the feed minus the volume of 1000° F.+ boiling material in the product (over that same period of time); this quantity is divided by the volume of 1000° F.+ boiling material in the feed, and the quantity is then multiplied by 100.

The choice of the operation conditions associated with a refinery in predicting the sediment content will be determined on whether the same hydroprocessing catalyst and amount thereof during hydroprocessing are used. For example, in the case of using the same catalyst and same catalyst amount, the at least two operation conditions associated with a refinery can be those discussed above, e.g., temperature, LHSV, conversion, cut point, etc. In one embodiment, the sediment content can be predicted according to the following exemplary formula:

$$S = X + X^1(\text{LHSV}) + X^2(T) + X^3(R) + X^4(A)$$

where S is the sediment content, LHSV represents the liquid hourly space velocity, T represents the temperature of the reactor, R is the asphaltene stability parameter, A is the asphaltene content and X, $X^1$, $X^2$, $X^3$ and $X^4$ are constants derived from linear regression.

In accordance with another embodiment, the method of the present invention further includes the step of generating a cost value for the first hydrocarbon-containing feedstock sample or the leading candidates for hydroprocessing. The cost value can be generated based on factors such as API gravity, sulfur content, vanadium and nickel contents, distillable material contents, viscosity, asphaltene content, Total Acid Number, etc. The cost value generated for the first hydrocarbon-containing feedstock sample can then be compared with a market price of the same or different hydrocarbon-containing feedstock. In this manner, one can determine if the one or more hydrocarbon-containing feedstocks tested in the methods described herein are comparable to their market price.

The information obtained from the methods of the present invention can then be stored in a relational database. For example, a relational database can be electrically connected to a signal data collector comprising a computer microprocessor for system operation and control to collect the data from the various tests over an extended period of time to compile a library therefrom. The database can be used to find optimum combinations for a desired product stream, and can be particularly useful when the desired product stream varies depending on market factors. When the product requirements change, appropriate combinations can be selected to prepare the desired product.

If desired, the selection of the one or more hydrocarbon-containing feedstocks can further employ one or more additional steps as discussed above, such as step (vii) selecting one or more second hydrocarbon-containing feedstock samples; repeating steps (i)-(vi); and comparing the results of the one or more second hydrocarbon-containing feedstock samples with the results of the first hydrocarbon-containing feedstock sample to predict one or more leading candidate hydroprocessed hydrocarbon-containing feedstocks.

In one embodiment, once one or more of the leading hydrocarbon-containing feedstock have been selected, one or more of the selected hydrocarbon-containing feedstock can then be used as a component for blending with one or more other selected hydrocarbon-containing feedstocks.

In one embodiment, once one or more of the hydrocarbon-containing feedstocks have been selected, one or more of the selected hydrocarbon-containing feedstocks or blends thereof can then be used as a refinery feedstock in one or more crude hydrocarbon refining components within a refinery and subjected to one or more conventional hydroprocessing techniques such as hydrotreating, hydrocracking, hydrogenation, hydrofinishing and hydroisomerization and the like. Alternatively, one or more of the selected hydrocarbon-containing feedstocks can be blended with one or more of the same or different hydrocarbon-containing feedstocks. The refinery hydroprocesses that the one or more of the selected hydrocarbon-containing feedstocks can be used in are well known in the art.

The term "crude hydrocarbon refinery component" generally refers to an apparatus or instrumentality of a process to refine crude hydrocarbons, such as an oil refinery process. Crude hydrocarbon refinery components include, but are not limited to, heat transfer components such as a heat exchanger, a furnace, a crude preheater, a coker preheater, or any other heaters, a FCC slurry bottom, a debutanizer exchanger/tower, other feed/effluent exchangers and furnace air preheaters in refinery facilities, flare compressor components in refinery facilities and steam cracker/reformer tubes in petrochemical facilities. Crude hydrocarbon refinery components can also include other instrumentalities in which heat transfer may take place, such as a fractionation or distillation column, a scrubber, a reactor, a liquid-jacketed tank, a pipestill, a coker and a visbreaker. It is understood that "crude hydrocarbon refinery components," as used herein, encompass tubes, piping, baffles and other process transport mechanisms that are internal to, at least partially constitute, and/or are in direct fluid communication with, any one of the above-mentioned crude hydrocarbon refinery components.

In one embodiment, representative examples of such crude hydrocarbon refinery components include a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank, a visbreaker and the like.

Accordingly, another embodiment of the present invention is directed to a method involving:

(a) selecting one or more hydrocarbon-containing feedstocks, wherein the selection of the one or more hydrocarbon-containing feedstocks comprises:

(i) precipitating an amount of asphaltenes from a liquid sample of a first hydrocarbon-containing feedstock having solvated asphaltenes therein with one or more first solvents in a column;

(ii) determining one or more solubility characteristics of the precipitated asphaltenes;

(iii) analyzing the one or more solubility characteristics of the precipitated asphaltenes;

(iv) determining asphaltene content of the liquid sample from the results of analyzing the one or more solubility characteristics of the precipitated asphaltenes;

(v) determining one or more asphaltene stability parameters of the liquid sample from the results of analyzing the one or more solubility characteristics of the precipitated asphaltenes; and (vi) correlating the asphaltene content and one of the asphaltene stability parameters of the liquid sample and at least two operation conditions associated with a refinery to predict sediment content of a hydroprocessed hydrocarbon product; and (b) feeding the selected one or more hydrocarbon-containing feedstocks to one or more crude hydrocarbon refinery components.

The following non-limiting examples are illustrative of the present invention.

EXAMPLE 1

Several different hydrocarbon-containing feedstocks were hydroprocessed in a pilot plant using the operation conditions set forth in Table 1. The sediment content of the hydroprocessed hydrocarbon products was then measured using ASTM 4870. First, solutions of the feedstocks were prepared by dissolving 0.1000 g of the material in 10 mL of methylene chloride. Then, the solutions were injected into a separate stainless steel column packed with poly(tetrafluoroethylene) (PTFE) using n-heptane as a mobile phase. The flow rate during the whole process was 4 mL/min. The maltenes (heptane solubles) eluted from the column as the first peak around 2 minutes after the injection.

The asphaltenes remained precipitated in the column and were fractionated according to their respective solubilities by switching the mobile phase in successive steps to solvents of increasing solubility parameters: (1) 10 minutes after the injection of the sample, the mobile phase was switched to a blend of 15% methylene chloride/85% n-heptane (Solubility Parameter of 16.05 MPa$^{0.5}$) (2) 20 minutes after the injection of the sample, the mobile phase was switched to a blend of 30% methylene chloride/70% n-heptane (Solubility Parameter of 18.8 MPa$^{0.5}$) (3) 30 minutes after the mobile phase was switched to 100% methylene chloride (Solubility Parameter of 20.3 MPa$^{0.5}$); and (4) 40 minutes after the injection of the sample, the mobile phase was switched to a blend of 10% methanol/90% methylene chloride (Solubility Parameter of 21.23 MPa$^{0.5}$). After 10 additional minutes, the solvent was switched again to n-heptane to prepare the column for the next sample. Four asphaltene fractions were obtained: (1) asphaltenes soluble in 85/15 heptane/methylene chloride (peak 1), (2) 70/30 heptane/methylene chloride (peak 2), (3) 100% methylene chloride (peak 3) and (4) 90/10 methylene chloride/methanol (peak 4). In this manner, four different asphaltenes solubility fractions were separated with a total analysis time of approximately 60 minutes.

The concentrations of maltenes and asphaltenes were quantified using an Evaporative Light Scattering Detector (ELSD) (Alltech ELSD 2000), which was equipped with a light-scattering photometer by evaporating the solvent and passing the stream containing non-volatile particles (asphaltenes or maltenes) through the light-scattering photometer. The ELSD operated at the following conditions: drift tube temperature 75° C.; volumetric flow of the solvents was 4 mL/min. and 3.5 L/min. of nitrogen as the nebulizing gas. The light scattered by the non-volatile particles was collected and is a measure of the concentration of the solute in the column effluent. The area under the obtained peaks was calculated using the commercial software Chemstation® by Agilent Technologies (Santa Clara, Calif.). Then, this area was correlated to an asphaltene mass according to a calibration curve.

The asphaltene stability, i.e., R values, were calculated according to the following equation:

$$R = (\text{Area peak 3} + \text{Area peak 4})/(\text{Area peak 1} + \text{Area peak 2})$$

The areas were also used to determine the asphaltene content as follows. Each area was correlated to an asphaltene mass according to a calibration curve that for the ELSD is as follows:

$$\log M_i = C \log A_i + B$$

wherein $M_i$ and $A_i$ are the mass and the area corresponding to the peak i with i varying from 1 to 4, and C and B are constants determined using the regression analysis tool available in Excel Software by Microsoft Co.

Next, the total asphaltene mass (TAM) for the sample was calculated by the addition of all the asphaltene masses ($M_i$) determined for each peak:

$$TAM = \sum_{i=1}^{4} M_i$$

TABLE 1

| Feed | Liquid Hourly Space Velocity (hr$^{-1}$) | Temperature of the reactor (° F.) | Conversion (wt. %) | Cut Point of the residue (° F.) | Sediment Content (ppm) |
|---|---|---|---|---|---|
| A | 0.27 | 810 | 85 | 975 | 190 |
| B | 0.15 | 774 | 72 | 1075 | 100 |
| B | 0.15 | 782 | 78 | 1075 | 1000 |
| B | 0.15 | 791 | 82 | 1075 | 2000 |
| C | 1.1 | 825 | 58 | 975 | 570 |
| D | 0.4 | 800 | 57 | 1000 | 1110 |
| D | 0.4 | 815 | 64 | 1000 | 2750 |
| E | 0.13 | 757 | 53 | 1050 | 500 |
| E | 0.13 | 773 | 76 | 1050 | 3500 |
| F | 0.17 | 795 | 76 | 1000 | 3600 |

Figure 1:
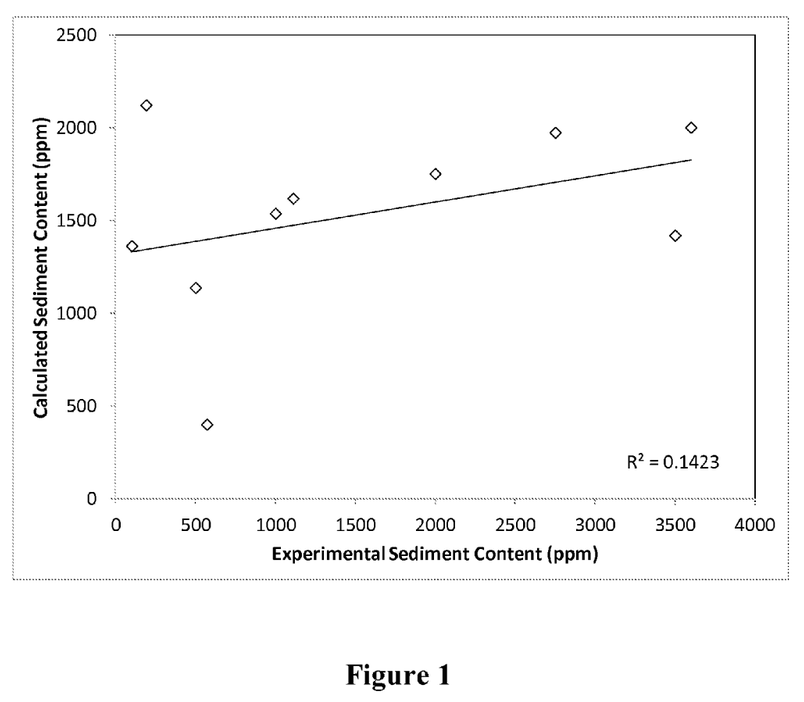
FIG. 1 shows a comparison between the sediment content calculated by equation (1) and the sediment content determined by ASTM 4870.

A first attempt was made to correlate the sediment content of the hydroprocessed feedstocks with the variables of refinery operation conditions without taking into consideration the characteristics of the feed, i.e., asphaltene content and asphaltene stability, using the following equation (1):

$$S = -16075 - 2759 \times LHSV + 26.62 \times T - 6.25 \times C - 2.14 \times Cut \quad (1)$$

where S is the sediment content, LHSV is the liquid hourly space velocity, T represents the temperature of the reactor, C is conversion, and Cut is the cut point of the residue. As can be seen in FIG. 1, the correlation obtained was poor ($R^2 = 0.1423$). The constants in the equation were obtained using a using a regression analysis tool available in Excel Software by Microsoft Co.

Figure 2:
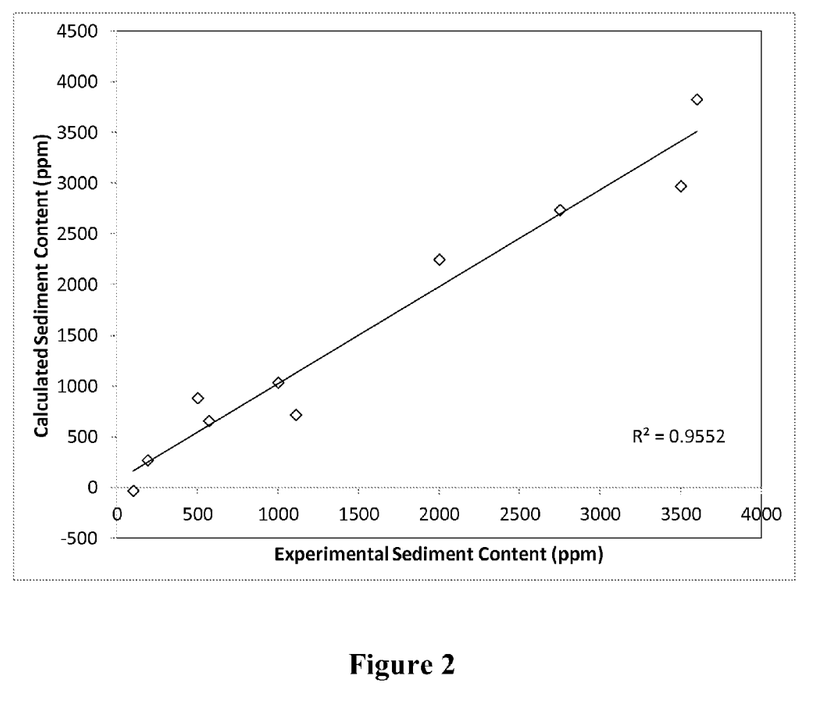
FIG. 2 shows a comparison between the sediment content calculated by equation (2) and the sediment content determined by ASTM 4870.

A second attempt was then made using asphaltene stability (determined as R) and asphaltene content of the feeds discussed above. The corresponding equation (2) was as follows:

$$S = -93730 - 4864 \times LHSV + 136 \times T - 4.08 \times C - 0.63 \times Cut - 2794 \times R - 475 \times Asp \quad (2)$$

where S is the sediment content, LHSV represents the liquid hourly space velocity, T represents the temperature of the reactor, C is conversion, Cut is cut point of the residue, R is the asphaltene stability and Asp is the asphaltene content determined for the feeds. The constants in the equation were obtained using a regression analysis methodology available in Excel Software by Microsoft Co. FIG. 2 shows a comparison between the sediment content calculated using equation (2) and the experimental sediment content determined by ASTM 4870. As can be seen, the correlation coefficient was $R^2 = 0.9552$.

Figure 3:
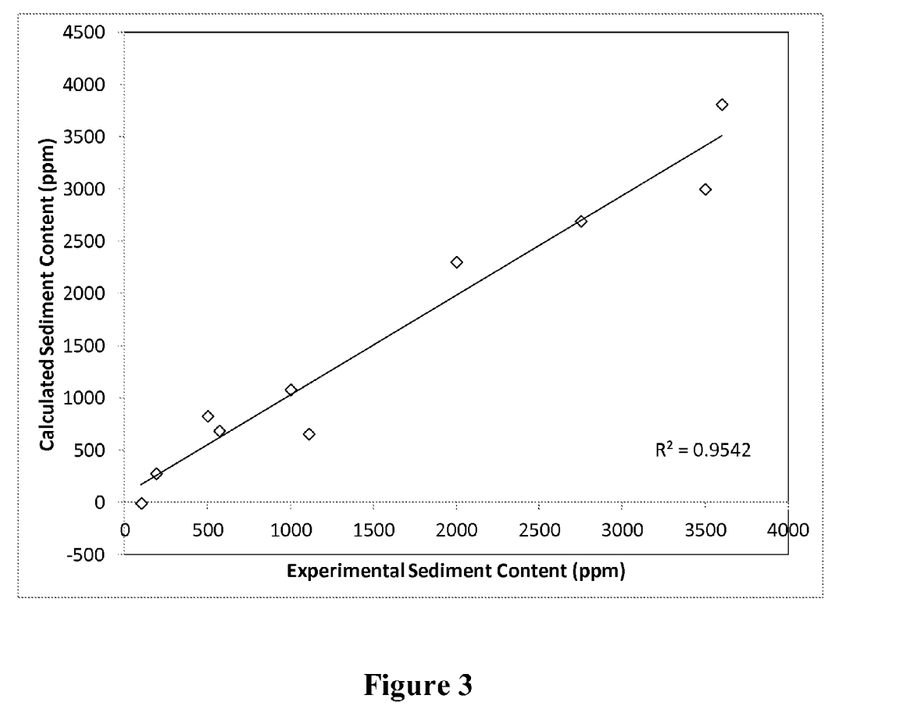
FIG. 3 shows a comparison between the sediment content calculated by equation (3) and the sediment content determined by ASTM 4870 for samples in Example 1.

In a further refinement, it was possible to obtain a correlation by removing some of the reaction variables that were correlated in equation (2). The corresponding equation (3) was as follows:

$$S = -94176.7 - 4697 \times LHSV + 136 \times T - 2797 \times R - 475 \times Asp \quad (3)$$

where S is the sediment content, LHSV represents the liquid hourly space velocity, T represents the temperature of the reactor, and R is the asphaltene stability and Asp is the asphaltene content determined for the feeds. As can be seen, the correlation coefficient was $R^2 = 0.9542$. The constants in the equation were obtained using a regression analysis methodology available in Excel Software by Microsoft Co.

FIG. 3 shows a comparison between the sediment content calculated using equation (3) and the experimental sediment content determined by ASTM 4870. These results indicate that sediment formation can be estimated using a combination of refinery operation condition variables and the characteristics of the feed, i.e., the asphaltene content and the stability.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method for predicting a sediment content of a hydroprocessed hydrocarbon product, the method comprising the steps of:
   (a) precipitating asphaltenes from a liquid sample of a first hydrocarbon-containing feedstock having solvated asphaltenes therein with one or more first solvents in a column;
   (b)
   (1)(i) dissolving at least part of a first amount of the precipitated asphaltenes from step (a) in one or more second solvents having a solubility parameter at least 0.7 MPa$^{0.5}$ higher than the solubility parameter of the one or more first solvents to provide a first eluted fraction of a first amount of the dissolved asphaltenes to determine one or more solubility characteristics of the first eluted fraction, and
   (1)(ii) dissolving a second amount of the precipitated asphaltenes from step (a) in one or more third solvents having a solubility parameter higher than the solubility parameter of the one or more second solvents, wherein the solubility parameter of the one or more third solvents is at least 21 MPa$^{0.5}$ but no greater than 30 MPa$^{0.5}$ to provide a second eluted fraction of the second amount of the dissolved asphaltenes to determine one or more solubility characteristics of the second eluted fraction; or
   (2) dissolving a first amount and a second amount of the precipitated asphaltenes from step (a) by gradually and continuously changing the one or more first solvents to a final mobile phase solvent having a solubility parameter at least 1 MPa$^{0.5}$ higher than the one or more first solvents to provide an eluted fraction of the dissolved asphaltenes to determine one or more solubility characteristics of the eluted fraction;
   (c) analyzing the one or more solubility characteristics of the precipitated asphaltenes, which comprises monitoring either an amount of the first eluted fraction and the second eluted fraction from step (b)(1), or an amount of the eluted fraction from step (b)(2), from the column with a liquid chromatography detector which generates a signal proportional to a concentration of the dissolved asphaltenes in either the first eluted fraction and the second eluted fraction from step (b)(1), or the eluted fraction from step (b)(2);
   (d) determining an asphaltene content of the liquid sample of the first hydrocarbon-containing feedstock from the analyzing step (c);
   (e) determining one or more asphaltene stability parameters of the liquid sample of the first hydrocarbon-containing feedstock from the analyzing step (c); and
   (f) correlating the asphaltene content and the one or more asphaltene stability parameters of the liquid sample of the first hydrocarbon-containing feedstock and at least two operation conditions associated with a refinery to predict the sediment content of the hydroprocessed hydrocarbon product such that based on the prediction,
   (1) refinery operation conditions can be adjusted in order to minimize fouling during hydroprocessing or
   (2) blending strategies of feedstocks can be designed and refinery operation conditions can be adjusted for further processing with minimal fouling or
   (3) quality control of new batches of feedstocks and in blending raw materials can be achieved without affecting refinery operation conditions.

2. The method of claim 1, wherein step (b) includes steps (b)(1)(i) and (b)(1)(ii), and further wherein the step of determining the asphaltene content comprises:
   calculating a peak area for each of the amounts of dissolved asphaltenes, wherein the peak area for each of the amounts of dissolved asphaltenes is derived from the signal generated by the liquid chromatography detector;
   correlating the peak area to an asphaltene mass; and
   adding each of the asphaltene masses (M) determined for each peak area to obtain a total asphaltene mass (TAM) according to the following equation:

$$TAM = \sum_{i=1}^{n} M_i$$

wherein M is the asphaltene mass determined for each peak area.

3. The method of claim 2, wherein the step of determining one or more asphaltene stability parameters comprises calculating a ratio for each eluted fraction according to the following equation:

Ratio=(area peak 3+area peak 4)/(area peak 1+area peak 2)

wherein area peak 1 is a first peak area characterizing a first eluted fraction eluted from the column, area peak 2 is a second peak area characterizing a second eluted fraction eluted from the column, area peak 3 is a third peak area characterizing a third eluted fraction eluted from the column and area peak 4 is a fourth peak area characterizing a fourth eluted fraction eluted from the column.

4. The method of claim 1, wherein step (b)(2) comprises:
   (i) gradually and continuously changing the one or more first solvents to a first final mobile phase solvent having a solubility parameter at least 1 MPa$^{0.5}$ higher than the solubility parameter of the one or more first solvents to dissolve the first amount of the precipitated asphaltenes to provide a first eluted fraction of the first amount of the dissolved asphaltenes; and
   (ii) gradually and continuously changing the first final mobile phase solvent to a second final mobile phase solvent having a solubility parameter at least 1 MPa$^{0.5}$ higher than the solubility parameter of the first final mobile phase solvent to dissolve the second amount of the precipitated asphaltenes to provide a second eluted fraction of the second amount of the dissolved asphaltenes.

5. The method of claim 4, wherein the step of determining asphaltene content comprises:
   calculating a peak area under an obtained second peak for the second amount of the dissolved asphaltenes, wherein the peak area is derived from the signal, correlating the peak area to an asphaltene mass; and
determining the Log TAM in the liquid sample of the first hydrocarbon-containing feedstock according to the following equation:

$$\text{Log TAM} = 0.5336 \log A - 6.097$$

where TAM is the total asphaltene mass and A is the area of each respective peak.

6. The method of claim 5, wherein the step of determining one or more asphaltene stability parameters comprises:
   (i) calculating an average solubility parameter of the second amount of the dissolved asphaltenes;
   (ii) calculating a ratio of the peak areas of the second amount of dissolved asphaltenes to the first amount of the dissolved asphaltenes, wherein each of the peak areas are derived from the signal; or
   (iii) calculating an overlapping area of the peak areas of the second amount of the dissolved asphaltenes and the first amount of the dissolved asphaltenes; or
   (iv) calculating the overlapping area of the peak areas of the second amount of the dissolved asphaltenes and the first amount of the dissolved asphaltenes, wherein each of the peak areas are derived from the signal; or
   (v) calculating $\Delta PS$ from a $\Delta PS$ equation:

$$\Delta PS = t(75\%) - t(25\%)$$

wherein $t(75\%)$ and $t(25\%)$ represent a time at which 75% and 25% of the asphaltenes in the liquid sample of the hydrocarbon-containing feedstock sample have eluted.

7. The method of claim 1, wherein the at least two operation conditions associated with the refinery are selected from the group consisting of a Liquid Hourly Space Velocity (LHSV), a temperature of a reactor, a % residue conversion, and a cut point of a residue.

8. The method of claim 7, wherein the sediment content of the hydroprocessed hydrocarbon product is predicted according to the following equation:

$$S = X + X^1(\text{LHSV}) + X^2(T) + X^3(R) + X^4(\text{Asp})$$

where S is the sediment content, LHSV represents the liquid hourly space velocity, T represents the temperature of the reactor, R is the asphaltene stability parameter, Asp is the asphaltene content and X, $X^1$, $X^2$, $X^3$ and $X^4$ are constants derived from linear regression.

9. The method of claim 1, further comprising the steps of
   (g) selecting one or more second hydrocarbon-containing feedstock samples; repeating steps (a)-(f); and
   (h) comparing the sediment content predicted in step (f) of the one or more second hydrocarbon-containing feedstock samples with the sediment content predicted in step (f) of the first hydrocarbon-containing feedstock sample to predict one or more leading candidate hydrocarbon-containing feedstocks for hydroprocessing.

* * * * *